United States Patent
Cho et al.

(10) Patent No.: US 10,776,365 B2
(45) Date of Patent: Sep. 15, 2020

(54) METHOD AND APPARATUS FOR CALCULATING SIMILARITY OF LIFE LOG DATA

(71) Applicant: AJOU UNIVERSITY INDUSTRY-ACADEMIC COOPERATION FOUNDATION, Suwon-si, Gyeonggi-do (KR)

(72) Inventors: We Duke Cho, Seongnam-si (KR); Kyu Pil Lee, Suwon-si (KR); Sun Taag Choe, Suwon-si (KR); Jong Ik Lee, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 502 days.

(21) Appl. No.: 15/655,430

(22) Filed: Jul. 20, 2017

(65) Prior Publication Data

US 2018/0052892 A1   Feb. 22, 2018

(30) Foreign Application Priority Data

Aug. 19, 2016 (KR) .................. 10-2016-0105553
Oct. 18, 2016 (KR) .................. 10-2016-0135076

(51) Int. Cl.
| | | |
|---|---|---|
| *G06F 16/30* | (2019.01) | |
| *G06F 16/2457* | (2019.01) | |
| *G06F 16/25* | (2019.01) | |
| *G06F 16/2458* | (2019.01) | |
| *G16H 40/63* | (2018.01) | |

(Continued)

(52) U.S. Cl.
CPC .... *G06F 16/24575* (2019.01); *G06F 16/2477* (2019.01); *G06F 16/24578* (2019.01); *G06F 16/258* (2019.01); *G16H 10/60* (2018.01); *G16H 40/63* (2018.01); *G16H 50/70* (2018.01)

(58) Field of Classification Search
CPC ................. G06F 16/24575; G06F 16/24578
See application file for complete search history.

(56) References Cited

U.S. PATENT DOCUMENTS

2013/0194066 A1* 8/2013 Rahman ................ G05B 1/01
340/5.51
2014/0335490 A1* 11/2014 Baarman ............... A61B 5/002
434/236

FOREIGN PATENT DOCUMENTS

KR   10-2009-0112349 A   10/2009

* cited by examiner

*Primary Examiner* — Thu Nguyet T Le
(74) *Attorney, Agent, or Firm* — Stein IP, LLC

(57) ABSTRACT

Disclosed are a method and an apparatus for calculating similarity of life log data, the method including: producing, by a life log data producing unit, a plurality of life log data on a daily basis, in which at least one estimated activity state is indicated for each predetermined time section, by matching a user's position information per time period and a user's motion state information per time period with an estimated activity table in which the user's estimated activity states are defined in advance; converting, by a modified life log data producing unit, the plurality of life logs data into a plurality of modified life log data which is indicated for each merged time section made by merging a preset number of continuous time sections; and calculating, by a similarity calculating unit, life log similarity among the plurality of modified life log data by comparing the plurality of modified life log data for each merged time section.

14 Claims, 11 Drawing Sheets

(51) Int. Cl.
*G16H 10/60* (2018.01)
*G16H 50/70* (2018.01)

[FIG. 1]
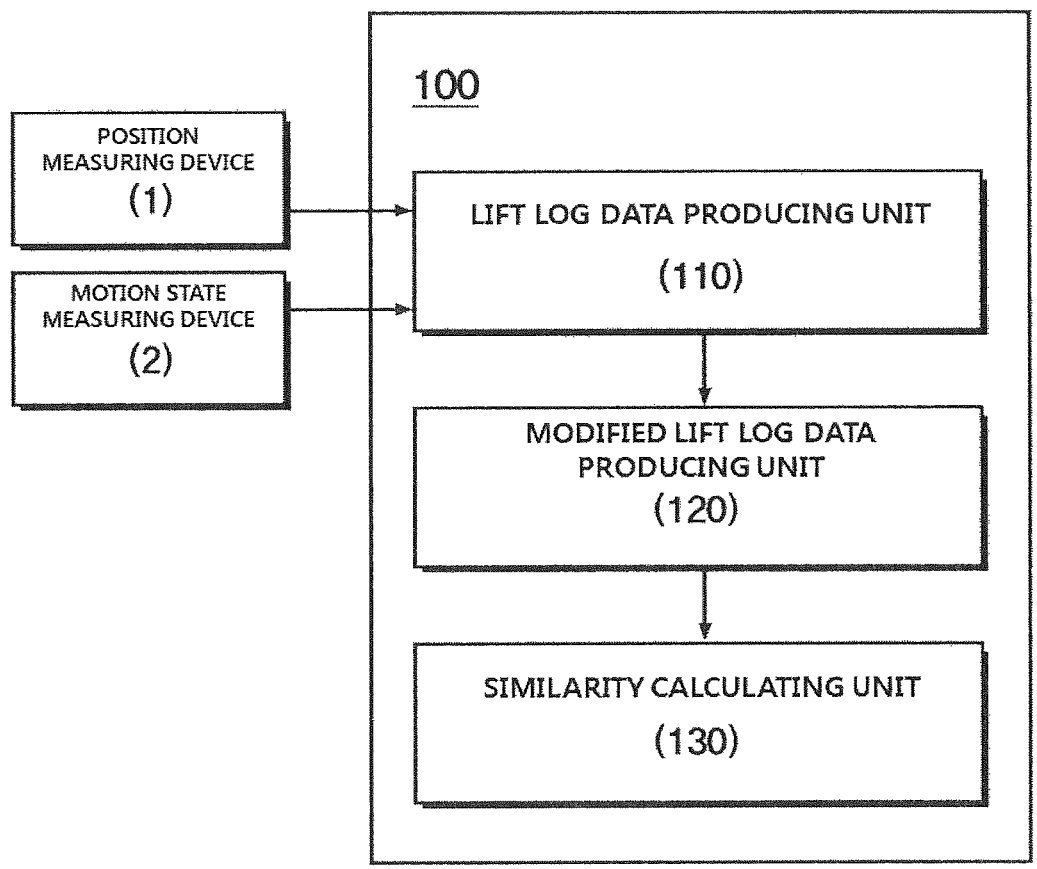

[FIG. 2]
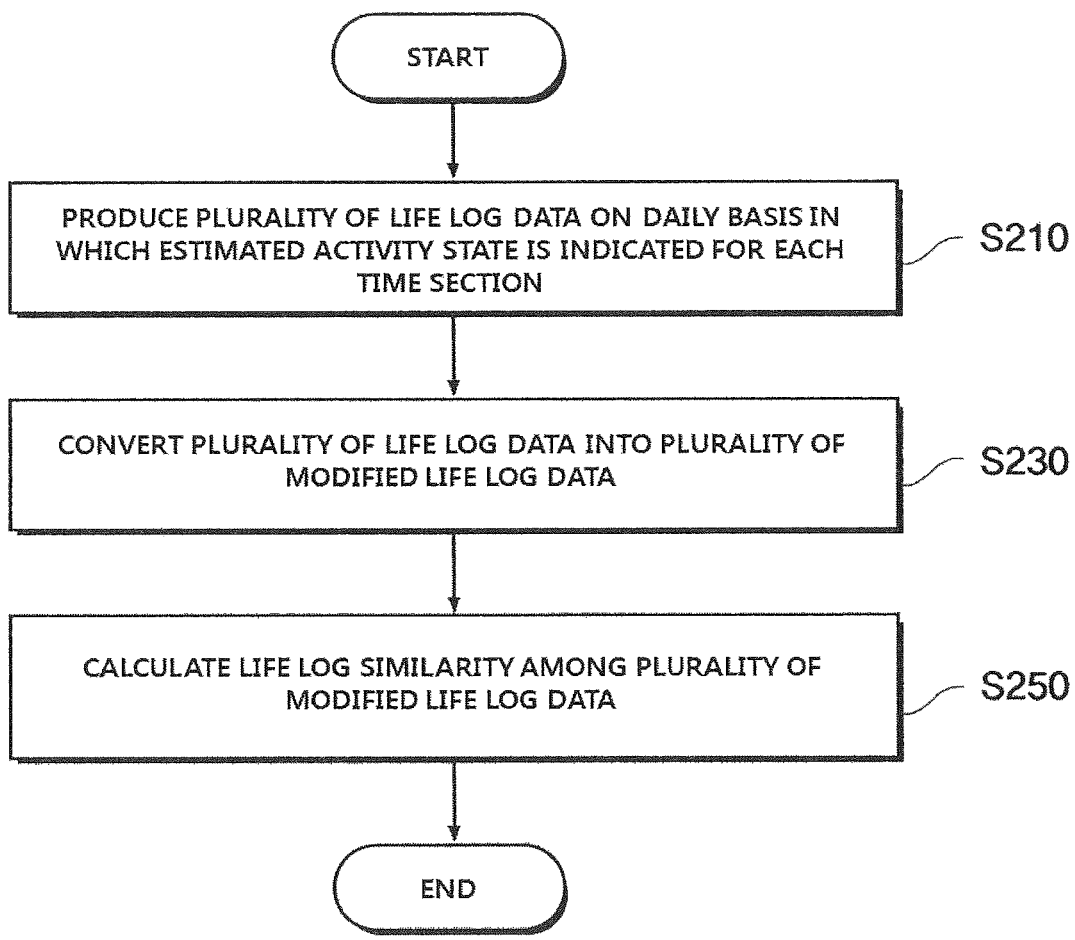

[FIG. 3]
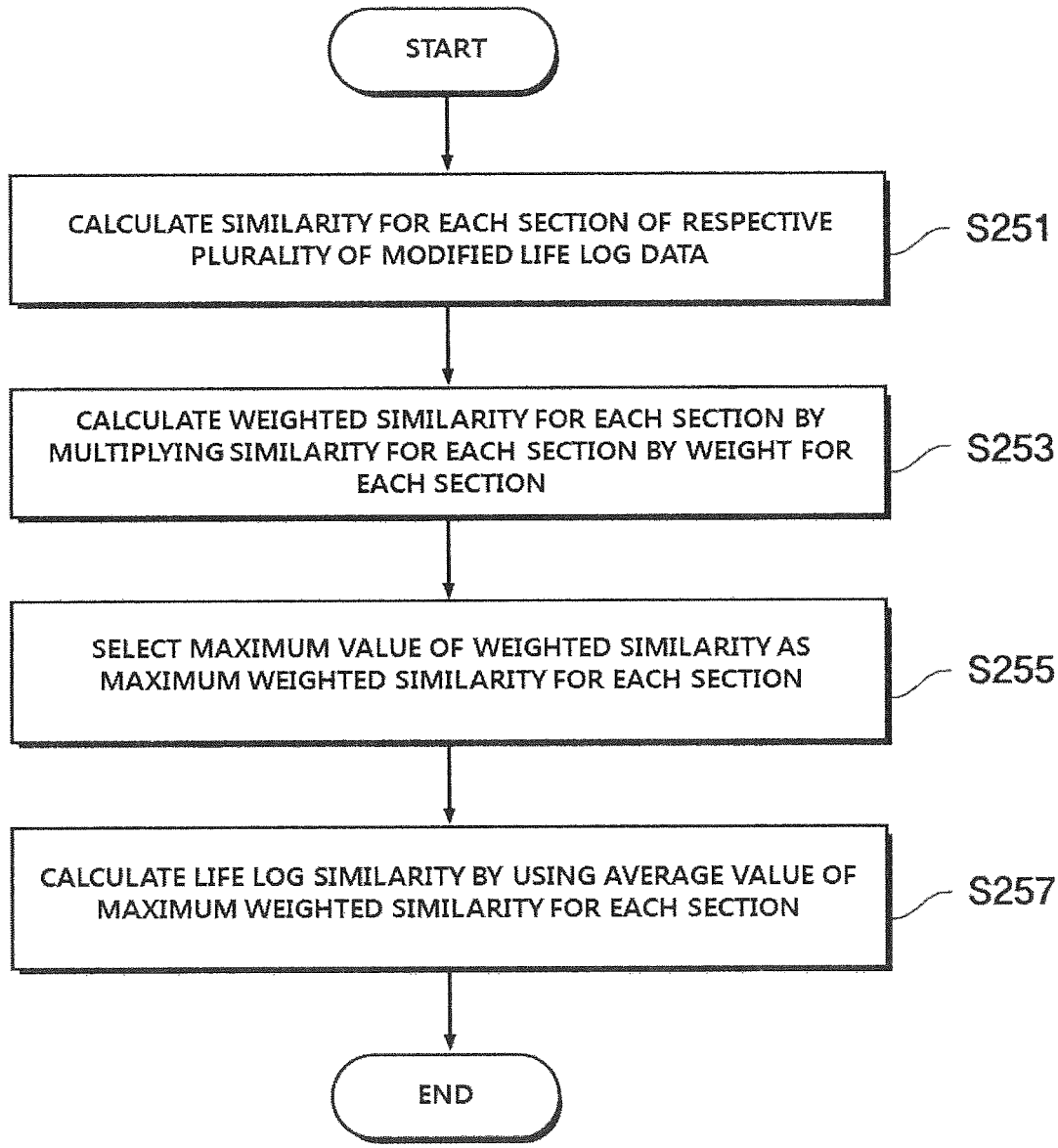

[FIG. 4]

| Idx | 1 | 2 | 3 | 4 | 5 | 6 | 7 | 8 | 9 |
|---|---|---|---|---|---|---|---|---|---|
| ESTIMATED ACTIVITY STATE | SLEEPING | STEADY | WALKING | RUNNING | REST | WORKING | EXERCISING | IN VEHICLE | LECTURE |

[FIG. 5]
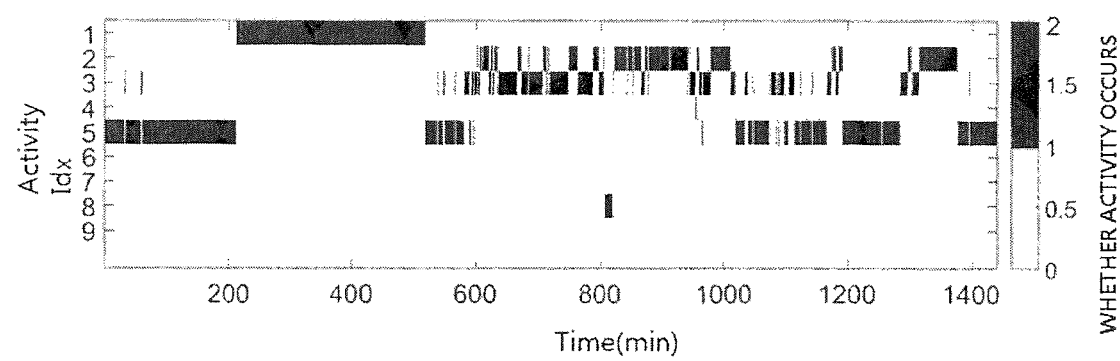

[FIG. 6]
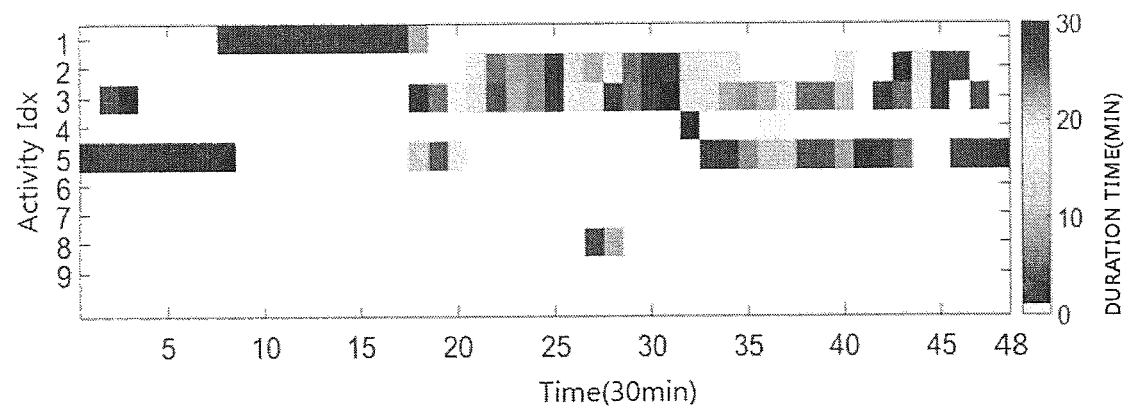

[FIG. 7]
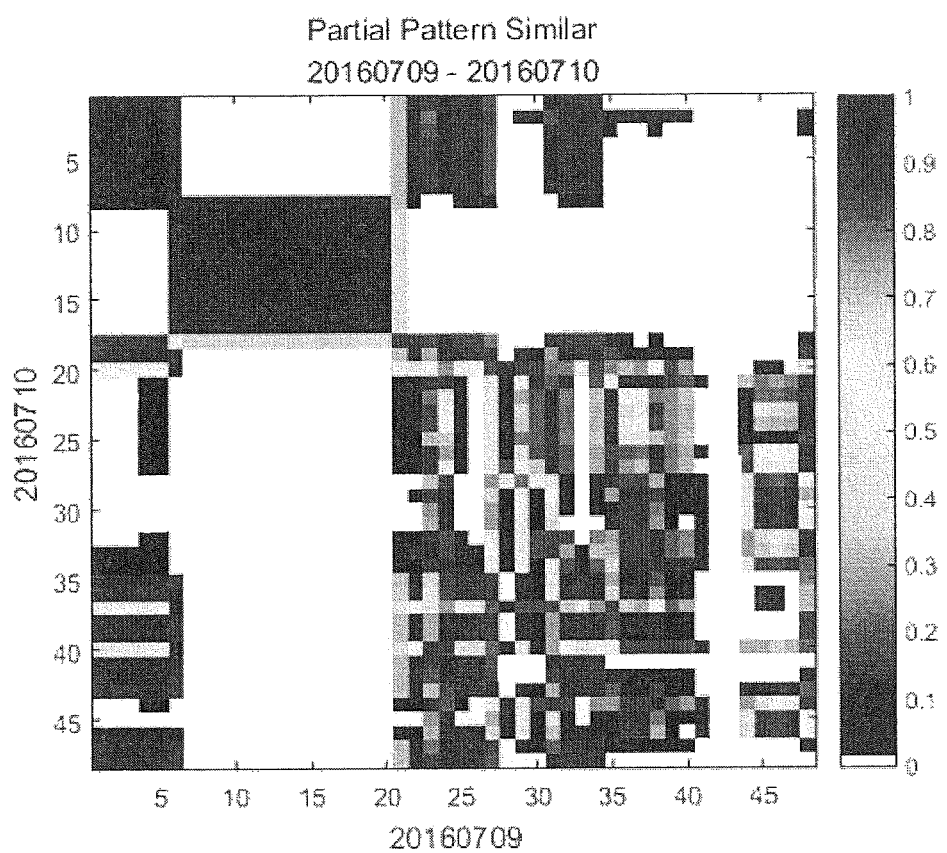

[FIG. 8]
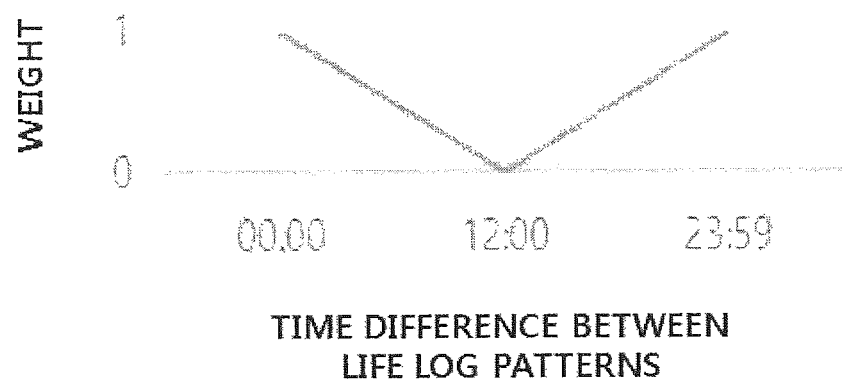
TIME DIFFERENCE BETWEEN
LIFE LOG PATTERNS

[FIG. 9]
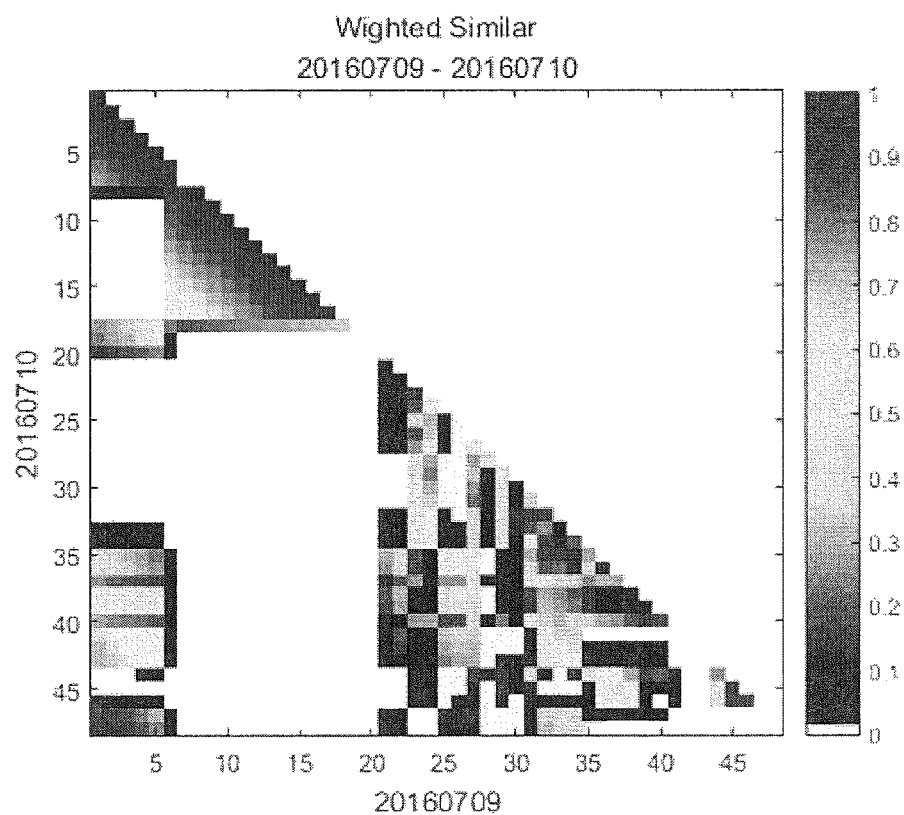

[FIG. 10]
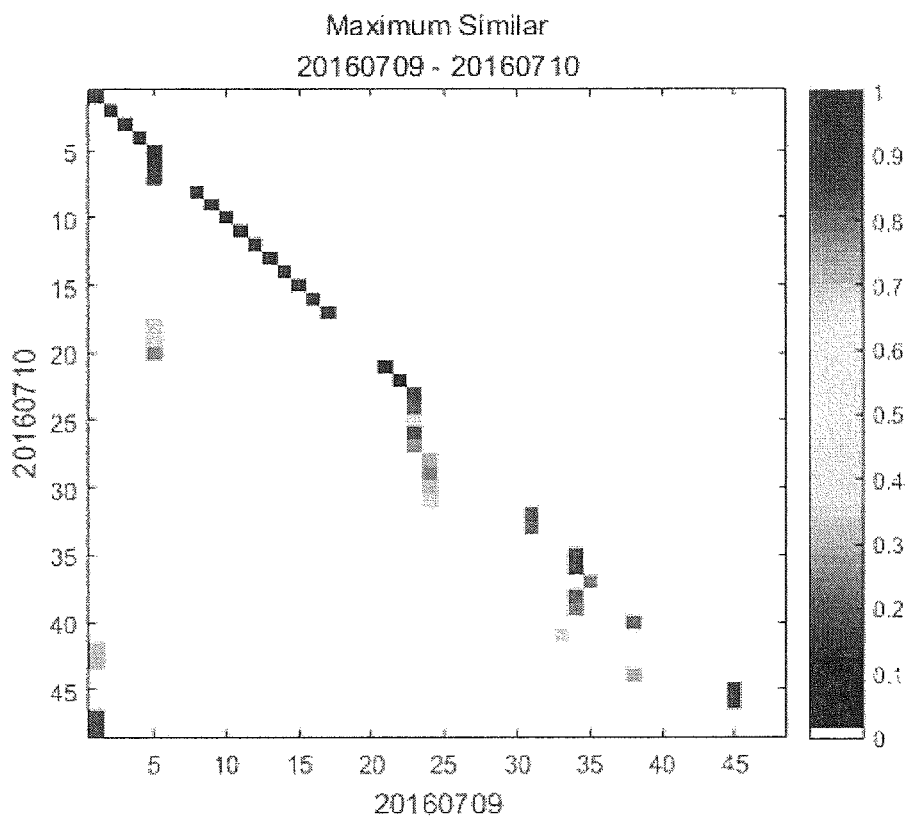

[FIG. 11]

SIMILARITY (UNIT : %)

| REFERENCE / COMPARISON OBJECT | DAY1 | DAY2 | DAY3 | DAY4 | DAY5 |
|---|---|---|---|---|---|
| DAY1 | 100.00 | 81.12 | 66.72 | 67.18 | 77.96 |
| DAY2 | 72.27 | 100.00 | 70.85 | 73.92 | 68.71 |
| DAY3 | 57.78 | 55.41 | 100.00 | 70.20 | 50.37 |
| DAY4 | 63.09 | 69.39 | 78.07 | 100.00 | 64.80 |
| DAY5 | 84.04 | 85.93 | 68.89 | 76.54 | 100.00 |

METHOD AND APPARATUS FOR CALCULATING SIMILARITY OF LIFE LOG DATA

CROSS-REFERENCE TO RELATED APPLICATIONS

This application claims the priority of Korean Patent Application Nos. 10-2016-0105553 filed on Aug. 19, 2016, 10-2016-0135076 filed on Oct. 18, 2016 in the Korean Intellectual Property Office, the disclosure of which is incorporated herein by reference.

BACKGROUND

Field

Exemplary embodiments of the present disclosure relate to a method and an apparatus for calculating similarity of life log data for calculating similarity among a plurality of life log data.

Description of the Related Art

Recently, various types of smart devices such as smart phones, smart pads, and tablet PCs come into wide use, and various types of auxiliary devices such as wearable devices, which operate in conjunction with the smart devices, also actively come into wide use.

The various types of smart devices and the various types of auxiliary devices include various types of functions such as GPS functions for recognizing position information of users, and activity intensity measuring functions for recognizing motion state information of users, such that the users may obtain various types of information such as their position information and their motion state information by utilizing the functions of the various types of smart devices and the various types of auxiliary devices.

In the related art, because the user obtains the various types of information individually from the respective devices, the user inevitably records the information obtained from the respective devices by writing in order to analyze and manage his/her lifestyle habit or the like, and as a result, there is a problem in that reliability of the recorded information deteriorates because the user depends on his/her memory.

To solve the aforementioned problem, a life log, in which a personal daily life is recorded by collecting various types of information obtained from the various types of smart devices and the various types of auxiliary devices, has been proposed, and thus the user may electronically record his/her daily life by utilizing the life log.

However, even though the user may easily record his/her daily life by utilizing the life log, there is a problem in that the user needs to ascertain his/her lifestyle habits and life patterns by directly comparing the plurality of life logs in order to ascertain his/her lifestyle habit and life patterns by using the plurality of life logs.

In particular, in view of statistical data regarding ten leading causes of death in Korea, six (cancer, heart diseases, cerebrovascular diseases, pneumonia, diabetes, and hypertension) of the ten leading causes of death in Korea are diseases associated with the lifestyle habit, and the world health organization (WHO) reported that the diseases associated with the lifestyle habit may be prevented just by managing the personal lifestyle habit, and as a result, it is important to recognize the user's lifestyle habit by comparing the plurality of life logs.

DOCUMENT OF RELATED ART

Patent Document

Korean Patent Application Laid-Open No. 10-2009-0112349 (Oct. 28, 2009)

SUMMARY

An object of the present disclosure is to solve the aforementioned problems, and to compare a plurality of life logs by calculating similarity among a plurality of modified life log data.

Technical problems of the present disclosure are not limited to the aforementioned technical problem, and other technical problems, which are not mentioned above, may be clearly understood by those skilled in the art from the following descriptions.

According to an aspect of the present disclosure, there is provided a method of calculating similarity of life log data, the method including: producing, by a life log data producing unit, a plurality of life log data on a daily basis, in which at least one estimated activity state is indicated for each predetermined time section, by matching a user's position information per time period and a user's motion state information per time period with an estimated activity table in which the user's estimated activity states are defined in advance; converting, by a modified life log data producing unit, the plurality of life logs data into a plurality of modified life log data which is indicated for each merged time section made by merging a preset number of continuous time sections; and calculating, by a similarity calculating unit, life log similarity among the plurality of modified life log data by comparing the plurality of modified life log data for each merged time section.

According to the exemplary embodiment, the motion state information may be information which indicates the user's motion state at a particular time which is selected based on the user's motion intensity, and the motion state information may include at least one state information among steady state information, sleeping state information, walking state information, and running state information.

For example, the modified life log data may be data that indicate estimated activity state vectors indicating a duration time of at least one estimated activity state for each merged time section.

For example, the calculating of the similarity may include: calculating similarity for each section which is similarity between the estimated activity state vectors of the respective plurality of modified life log data in respect to identical merged time sections and different merged time sections of the respective plurality of modified life log data; selecting a maximum value of the similarity for each section as maximum similarity for each section for each merged time section based on any one of the merged time sections; and calculating the life log similarity by using an average value of the selected maximum similarity for each section.

According to the exemplary embodiment, the calculating of the similarity may include: calculating similarity for each section which is similarity between the estimated activity state vectors of the respective plurality of modified life log data in respect to identical merged time sections and different merged time sections of the respective plurality of modified life log data; calculating weighted similarity for each section by multiplying the similarity for each section by a preset weight for each section; selecting a maximum value of the weighted similarity for each section as maximum weighted similarity for each section for each merged time section based on any one of the merged time sections; and calculating the life log similarity by using an average value of the selected weighted maximum similarity for each section.

For example, the similarity for each section may be calculated based on cosine similarity between the estimated activity state vectors of the respective plurality of modified life log data.

According to the exemplary embodiment, the preset weight for each section may be set based on a time difference among the merged time sections of the respective plurality of modified life log data.

For example, the preset weight for each section may have a minimum value in a case in which the time difference between the merged time sections of the respective plurality of modified life log data is 12 hours, and have a maximum value in a case in which the time difference is 0 hour or 23 hours 59 minutes, and the preset weight for each section may be increased linearly or nonlinearly when the time difference between the merged time sections is decreased to 0 hour based on 12 hours or increased to 23 hours 59 minutes based on 12 hours.

According to the exemplary embodiment, the modified life log data may be data that indicate the respective estimated activity states by dividing the respective estimated activity states to preset colors based on a duration time of at least one estimated activity state for each merged time section.

For example, the estimated activity state may include a plurality of detailed estimated activity states divided based on at least one additional information among weather information, temperature information, humidity information, illumination intensity information, carbon dioxide amount information, and the user's heart rate information.

According to another aspect of the present disclosure, there is provided an apparatus for calculating similarity of life log data, the apparatus including: a life log data producing unit which produces a plurality of life log data on a daily basis, in which at least one estimated activity state is indicated for each predetermined time section, by matching a user's position information per time period and a user's motion state information per time period with an estimated activity table in which the user's estimated activity states are defined in advance; a modified life log data producing unit which converts the plurality of life logs data into a plurality of modified life log data which is indicated for each merged time section made by merging a preset number of continuous time sections; and a similarity calculating unit which calculates life log similarity among the plurality of modified life log data by comparing the plurality of modified life log data for each merged time section.

For example, the modified life log data may be data that indicate estimated activity state vectors indicating duration times of at least one estimated activity state for each merged time section.

According to the exemplary embodiment, the similarity calculating unit may calculate similarity for each section which is similarity between the estimated activity state vectors of the respective plurality of modified life log data in respect to identical merged time sections and different merged time sections of the respective plurality of modified life log data, select a maximum value of the similarity for each section as maximum similarity for each section for each merged time section based on any one of the merged time sections, and calculate the life log similarity by using an average value of the selected maximum similarity for each section.

For example, the similarity calculating unit may calculate similarity for each section which is similarity between the estimated activity state vectors of the respective plurality of modified life log data in respect to identical merged time sections and different merged time sections of the respective plurality of modified life log data, calculate weighted similarity for each section by multiplying the similarity for each section by a preset weight for each section, select a maximum value of the weighted similarity for each section as maximum weighted similarity for each section for each merged time section based on any one of the merged time sections, and calculate the life log similarity by using an average value of the selected weighted maximum similarity for each section.

According to the exemplary embodiment, the preset weight for each section may be set based on a time difference among the merged time sections of the respective plurality of modified life log data.

According to the exemplary embodiment of the present disclosure, the plurality of life logs is compared with each other by calculating similarity between the plurality of modified life log data, and as a result, it is possible to recognize the user's lifestyle habit by using the life logs at another date which are similar to the life log of the user at a particular date.

BRIEF DESCRIPTION OF THE DRAWINGS

The above and other aspects, features and other advantages of the present disclosure will be more clearly understood from the following detailed description taken in conjunction with the accompanying drawings, in which:

FIG. 1 is a configuration diagram for explaining an apparatus for calculating similarity of life log data according to an exemplary embodiment of the present disclosure;

FIG. 2 is a flowchart for explaining a method for calculating similarity of life log data according to the exemplary embodiment of the present disclosure;

FIG. 3 is a flowchart for explaining a step of calculating life log similarity among a plurality of modified life log data in the method for calculating similarity of life log data according to the exemplary embodiment of the present disclosure;

FIG. 4 is a view for explaining an exemplary embodiment of an estimated activity table in the method and the apparatus for calculating similarity of life log data according to the exemplary embodiment of the present disclosure;

FIG. 5 is a view for explaining an exemplary embodiment of life log data produced by the method and the apparatus for calculating similarity of life log data according to the exemplary embodiment of the present disclosure;

FIG. 6 is a view for explaining an exemplary embodiment of modified life log data converted by the method and the apparatus for calculating similarity of life log data according to the exemplary embodiment of the present disclosure;

FIG. 7 is a view for explaining an exemplary embodiment of similarity for each section calculated by the method and the apparatus for calculating similarity of life log data according to the exemplary embodiment of the present disclosure;

FIG. 8 is a view for explaining an exemplary embodiment of a weight for each section in the method and the apparatus for calculating similarity of life log data according to the exemplary embodiment of the present disclosure;

FIG. 9 is a view for explaining an exemplary embodiment of weighted similarity for each section calculated by the method and the apparatus for calculating similarity of life log data according to the exemplary embodiment of the present disclosure;

FIG. 10 is a view for explaining an exemplary embodiment of maximum weighted similarity for each section selected by the method and the apparatus for calculating similarity of life log data according to the exemplary embodiment of the present disclosure; and FIG. 11 is a view for explaining life log similarity among a plurality of life log data compared by the method and the apparatus for calculating similarity of life log data according to the exemplary embodiment of the present disclosure.

DETAILED DESCRIPTION OF THE PREFERRED EMBODIMENT

Hereinafter, the exemplary embodiments of the present disclosure will be described with reference to the accompanying drawings in detail so that those skilled in the art may easily carry out the present disclosure. First, when reference numerals refer to constituent elements of each drawing, it should be noted that although the same constituent elements are illustrated in different drawings, the same constituent elements are referred to by the same reference numerals as possible. Further, in the following description of the present disclosure, a detailed description of publicly known configurations or functions incorporated herein will be omitted when it is determined that the detailed description may make the subject matter of the present disclosure unclear.

Hereinafter, a method and an apparatus for calculating similarity of life log data according to an exemplary embodiment of the present disclosure will be described in detail with reference to the accompanying drawings.

FIG. 1 is a configuration diagram for explaining the apparatus for calculating similarity of life log data according to the exemplary embodiment of the present disclosure.

As illustrated in FIG. 1, apparatus 100 for calculating similarity of life log data according to the exemplary embodiment of the present disclosure includes a life log data producing unit 110, a modified life log data producing unit 120, and a similarity calculating unit 130.

According to the exemplary embodiment, the apparatus 100 for calculating similarity of life log data according to the exemplary embodiment of the present disclosure, which is illustrated in FIG. 1, is illustrated as a separate apparatus that receives a particular user's position information per time period measured by a position measuring device 1 and particular user's motion state information per time period measured by a motion state measuring device 2. However, in addition to this, the apparatus 100 for calculating similarity of life log data according to the exemplary embodiment of the present disclosure may mean a partial configuration of the position measuring device 1 which is included in the position measuring device 1 and receives the particular user's motion state information per time period measured by the motion state measuring device 2, or may mean a partial configuration of the motion state measuring device 2 which is included in the motion state measuring device 2 and receives the particular user's position information per time period measured by the position measuring device 1.

For example, the position measuring device 1 may mean various types of devices such as smart phones, smart pads, tablet PCs, smart watches, and various types of wearable devices which support various types of functions such as GPS functions and Internet functions and measure the particular user's position information per time period.

For example, the motion state measuring device 2 may mean various types of devices such as smart phones, smart pads, tablet PCs, smart watches, and various types of wearable devices which include various types of sensors such as an acceleration sensor and a gravity sensor, measure the particular user's motion intensity per time period, and estimate the particular user's motion state per time period based on a magnitude value of the measured motion intensity, thereby producing the particular user's motion state information per time period.

For example, the motion state measuring device 2 may produce the particular user's motion state information at a particular time by applying one or more threshold values to a magnitude of the particular user's motion intensity per time period.

For example, the particular user's motion state information at a particular time may mean various types of motion state information such as sleeping state information in a state in which the user is sleeping, walking state information in a state in which the user is walking, running state information in a state in which the user is running, and steady state information in a state in which the user is not sleeping or moving, which may be estimated based on the user's motion intensity.

For example, a method of estimating the user's motion state by utilizing the user's motion intensity by means of the motion state measuring device 2 may be performed by utilizing various types of methods publicly known in the related art, and a specific description will be omitted.

According to the exemplary embodiment, in a case in which various types of devices such as smart phones, smart pads, tablet PCs, smart watches, and various types of wearable devices are devices capable of collecting both of the user's position information per time period and the motion state information per time period, the position measuring device 1 and the motion state measuring device 2 may be included in a single device.

For example, in a case in which the position measuring device 1 or the motion state measuring device 2 is a device such as smart phones, smart pads, tablet PCs, smart watches, and various types of wearable devices which may collect various types of environment information such as weather information, temperature information, humidity information, illumination intensity information, and carbon dioxide amount information, and may further collect various types of user biological information such as the user's heart rate information and various types of other information such as the user's meal time, the number of times of meals, a smoking status, a smoking time, or the number of times of smoking, the apparatus 100 for calculating similarity of life log data according to the exemplary embodiment of the present disclosure may calculate life log similarity among the plurality of life log data by further utilizing the various types of environment information, the various types of user biological information, and the various types of other information.

Now, the apparatus 100 for calculating similarity of life log data according to the exemplary embodiment of the present disclosure will be described still with reference to FIG. 1.

The life log data producing unit 110 produces a plurality of life log data on a daily basis, in which at least one estimated activity state is indicated for each predetermined time section, by matching the user's position information per time period and the motion state information per time period with an estimated activity table in which the user's estimated activity states are defined in advance.

The modified life log data producing unit 120 converts the plurality of life log data into a plurality of modified life log data which is indicated for each merged time section made by merging a preset number of continuous time sections.

For example, the modified life log data may be data that indicate estimated activity state vectors indicating duration times of at least one estimated activity state for each merged time section.

The similarity calculating unit 130 calculates life log similarity among the plurality of modified life log data by comparing the plurality of modified life log data for each merged time section.

According to the exemplary embodiment, the similarity calculating unit 130 may calculate similarity for each section which is similarity among estimated activity state vectors of the respective plurality of modified life log data in respect to identical merged time sections and different merged time sections of the plurality of modified life log data, may select a maximum value of the similarity for each section, as maximum similarity for each section, for each merged time section based on any one merged time section, and may calculate the life log similarity by using an average value of the selected maximum similarity for each section.

For example, the similarity calculating unit 130 may calculate the similarity for each section which is the similarity among the estimated activity state vectors of the respective plurality of modified life log data in respect to the identical merged time sections and the different merged time sections of the respective plurality of modified life log data, may calculate weighted similarity for each section by multiplying the similarity for each section by a preset weight for each section, may select a maximum value of the weighted similarity for each section, as maximum weighted similarity for each section, for each merged time section based on any one merged time section, and may calculate the life log similarity by using an average value of the selected maximum weighted similarity for each section.

According to the exemplary embodiment, the preset weight for each section may be set based on a time difference among the merged time sections of the respective plurality of modified life log data.

The exemplary embodiments of the respective constituent elements of the apparatus 100 for calculating similarity of life log data according to the exemplary embodiment of the present disclosure will be more specifically described below with reference to FIGS. 2 to 10, and the overlapping description thereof will be omitted.

FIG. 2 is a flowchart for explaining a method for calculating similarity of life log data according to the exemplary embodiment of the present disclosure.

As illustrated in FIG. 2, the method for calculating similarity of life log data according to the exemplary embodiment of the present disclosure includes step S210 of producing the plurality of life log data on a daily basis in which the estimated activity state is indicated for each time section, step S230 of converting the plurality of life log data into the plurality of modified life log data, and step S250 of calculating the life log similarity among the plurality of modified life log data.

In S210, the life log data producing unit 110 produces the plurality of life log data on a daily basis, in which at least one estimated activity state is indicated for each predetermined time section, by matching the user's position information per time period and the motion state information per time period with the estimated activity table in which the user's estimated activity states are defined in advance.

According to the exemplary embodiment, the position information per time period may mean position information per time period in respect to various types of places, where the particular user is positioned at a particular time, which is measured by the position measuring device 1.

For example, the motion state information is information regarding a user's motion state at a particular time which is selected based on user's motion intensity, and the motion state information may include at least one state information among the steady state information, the sleeping state information, the walking state information, and the running state information.

For example, the steady state information may mean the motion state information that indicates a state in which there is no motion of the particular user.

According to the exemplary embodiment, the steady state information may mean the user's motion state information which is not included in any one of the sleeping state information, the walking state information, and the running state information among the user's motion state information.

For example, the sleeping state information may mean the motion state information in respect to the particular user's sleeping state selected based on the motion intensity measured in a state in which the user is sleeping.

For example, the walking state information may mean the motion state information in respect to the particular user's walking state selected based on the motion intensity measured in a state in which the user is walking.

According to the exemplary embodiment, the running state information may mean the motion state information in respect to the particular user's running state selected based on the motion intensity measured in a state in which the user is running.

Now, the description of the estimated activity table and the method of matching the user's position information per time period and the motion state information per time period with the estimated activity table will be continued with reference to FIGS. 2 and 4 together, in step S210, as an example in which the number of estimated activity states is 9.

FIG. 4 is a view for explaining an exemplary embodiment of the estimated activity table in the method and the apparatus for calculating similarity of life log data according to the exemplary embodiment of the present disclosure.

According to the exemplary embodiment, as illustrated in FIG. 4, in a case in which the number of estimated activity states is 9, the estimated activity table may include at least one state among a sleeping state which is a first estimated activity state, a steady state which is a second estimated activity state, a walking state which is a third estimated activity state, a running state which is a fourth estimated activity state, a rest state which is a fifth estimated activity state, a working state which is a sixth estimated activity state, an exercising state which is a seventh estimated activity state, a vehicle boarding state which is an eighth estimated activity state, a lecture state which is a ninth estimated activity state.

For example, in a case in which the particular user's motion state information at a particular time, which is received by the life log data producing unit 110 from the motion state measuring device 2, is the sleeping state information, the life log data producing unit 110 may match the particular user's sleeping state information at a particular time with the sleeping state which is the first estimated activity state of the estimated activity table, thereby estimating that the particular user is in the sleeping state at a particular time.

According to the exemplary embodiment, in a case in which the particular user's motion state information at a particular time, which is received by the life log data producing unit 110 from the motion state measuring device 2, is the steady state information, the life log data producing unit 110 may match the particular user's steady state information at a particular time with the steady state which is the second estimated activity state of the estimated activity table, thereby estimating that the particular user is in the steady state in which the particular user is not moving at a particular time.

According to the exemplary embodiment, in a case in which the particular user's motion state information at a particular time, which is received by the life log data producing unit 110 from the motion state measuring device 2, is the walking state information, the life log data producing unit 110 may match the particular user's walking state information at a particular time with the walking state which is the third estimated activity state of the estimated activity table, thereby estimating that the particular user is in a state in which the particular user is walking at a particular time.

For example, in a case in which the particular user's motion state information at a particular time, which is received by the life log data producing unit 110 from the motion state measuring device 2, is the running state information, the life log data producing unit 110 may match the particular user's running state information at a particular time with the running state which is the fourth estimated activity state of the estimated activity table, thereby estimating that the particular user is in a state in which the particular user is running at a particular time.

According to the exemplary embodiment, in a case in which the particular user's position information at a particular time, which is received by the life log data producing unit 110 from the position measuring device 1, coincides with the particular user's home position information stored in advance and the particular user's motion state information at a particular time, which is received from the motion state measuring device 2, is the steady state information, the life log data producing unit 110 may match the particular user's position information and the particular user's motion state information at a particular time with the rest state which is the fifth estimated activity state of the estimated activity table, thereby estimating that the particular user is in a state in which the particular user takes a rest at home at a particular time.

According to the exemplary embodiment, in a case in which the particular user's position information at a particular time, which is received by the life log data producing unit 110 from the position measuring device 1, coincides with position information of the particular user's workplace which is stored in advance and the particular user's motion state information at a particular time, which is received from the motion state measuring device 2, is the steady state information, the life log data producing unit 110 may match the particular user's position information and the particular user's motion state information at a particular time with the working state which is the sixth estimated activity state of the estimated activity table, thereby estimating that the particular user is in a state in which the particular user is at work at the workplace at a particular time.

For example, in a case in which the particular user's position information at a particular time, which is received by the life log data producing unit 110 from the position measuring device 1, coincides with position information of a gymnasium used by the particular user which is stored in advance, the life log data producing unit 110 may match the particular user's position information at a particular time with the exercising state which is the seventh estimated activity state of the estimated activity table, thereby estimating that the particular user is in a state in which the particular user takes exercise in the gymnasium at a particular time.

According to the exemplary embodiment, in a case in which position information, which corresponds to the particular user's position information at a particular time which is received by the life log data producing unit 110 from the position measuring device 1, is not stored, the particular user's position information at a particular time is position information regarding an outdoor place, and the particular user's motion state information at a particular time, which is received from the motion state measuring device 2, is the steady state information, the life log data producing unit 110 may match the particular user's position information and the particular user's motion state information at a particular time with the vehicle boarding state which is the eighth estimated activity state of the estimated activity table, thereby estimating that the particular user is in a state in which the particular user is getting in the vehicle at the outdoor place at a particular time.

According to the exemplary embodiment, in a case in which the particular user's position information at a particular time, which is received by the life log data producing unit 110 from the position measuring device 1, coincides with position information of a school which the particular user attends which is stored in advance and the particular user's motion state information at a particular time, which is received from the motion state measuring device 2, is the steady state information, the life log data producing unit 110 may match the particular user's position information and the particular user's motion state information at a particular time with the lecture state which is the ninth estimated activity state of the estimated activity table, thereby estimating that the particular user is in a state in which the particular user is attending a lecture in the school at a particular time.

In addition to the nine examples in respect to the estimated activity states, the life log data producing unit 110 may further estimate various types of estimated activity states of the particular user such as estimating that the particular user is in a state in which the particular watches a movie in a movie theater at a particular time in a case in which the particular user's position information at a particular time coincides with position information of the movie theater which is stored in advance and the motion state information is the steady state information.

For example, the life log data producing unit 110 may estimate various types of estimated activity states of the particular user at a particular time which may be estimated based on the user's position information per time period and the user's motion state information per time period, and the estimated activity states according to the exemplary embodiment of the present disclosure are not limited to the nine states illustrated in FIG. 4.

According to the exemplary embodiment, in step S210, the life log data producing unit 110 may produce the plurality of life log data on a daily basis which indicates the result of matching the user's position information per time period and the user's motion state information per time period with the estimated activity table for each predetermined time section in a time series manner.

Now, the life log data, which is produced by the life log data producing unit 110 in step S210 in a case in which the number of estimated activity states is 9 and a predetermined time section for producing the life log data is one minute, will be described with reference to FIGS. 2 and 5 together.

FIG. 5 is a view for explaining an exemplary embodiment of the life log data produced by the method and the apparatus for calculating similarity of life log data according to the exemplary embodiment of the present disclosure.

As illustrated in FIG. 5, the life log data according to the exemplary embodiment of the present disclosure may be data in which a horizontal axis is set to a time axis having an interval of one minute, and a vertical axis is set to the first to ninth estimated activity states.

According to the exemplary embodiment, the life log data producing unit 110 may produce the plurality of life log data on a daily basis, and in this case, the respective life log data may have a total of 1,440 time sections because there are a total of 1,440 minutes in a day.

For example, as illustrated in FIG. 5, the life log data may be data that indicate the particular user's estimated activity states for the particular time section.

As illustrated in FIG. 5, in the exemplary embodiment of the life log data, a particular user's estimated activity state in a 200th time section may mean the rest state which is the fifth estimated activity state, and similarly, a particular user's estimated activity state in a 400th time section may mean the sleeping state which is the first estimated activity state.

According to the exemplary embodiment, in step S210, the life log data producing unit 110 my produce daily life log data at particular dates and daily life log data at other dates.

Now, step S230 will be described still with reference to FIG. 2.

In step S230, the modified life log data producing unit 120 converts the plurality of life log data into the plurality of modified life log data which is indicated for each merged time section made by merging a preset number of continuous time sections.

For example, the reason why step S230 is performed is that in a case in which similarity is calculated (S250) in order to compare the first life log data, which are the life log data at the particular dates, and the second life log data which are the life log data at other dates among the plurality of life log data, and in a case in which similarity between the entire data of the first life log data and the entire data of the second life log data is calculated, similarity for each estimated activity state may be calculated, but similarity in respect to transition information between the estimated activity states may not be calculated, and a calculation process is complicated in a case in which similarity between the data for the respective time sections of the first life log data and the data for the respective time sections of the second life log data is calculated.

Now, the exemplary embodiment, in which in S230 step, the modified life log data producing unit 120 produces the modified life log data having a total of 48 merged time sections by merging thirty continuous time sections in the life log data having 1,440 time sections illustrated in FIG. 5, will be described with reference to FIGS. 2 and 6 together.

FIG. 6 is a view for explaining the exemplary embodiment of the modified life log data converted by the method and the apparatus for calculating similarity of life log data according to the exemplary embodiment of the present disclosure.

As illustrated in FIG. 6, the modified life log data according to the exemplary embodiment of the present disclosure may be data in which a horizontal axis is set to a time axis having intervals of thirty minutes, and a vertical axis is set to the first to ninth estimated activity states.

According to the exemplary embodiment, the modified life log data producing unit 120 may produce the plurality of modified life log data on a daily basis, and in a case in which the horizontal axis is set to the time axis having intervals of thirty minutes, the modified life log data may have a total of 48 merged time sections.

For example, in a case in which in the modified life log data produced by the modified life log data producing unit 120, the horizontal axis is set to a time axis having intervals of one hour, the modified life log data may have a total of 24 merged time sections, and the present disclosure is not limited to a size of the merged time section.

As illustrated in FIG. 6, because the modified life log data produced by the modified life log data producing unit 120 are data in which the life log data are indicated for each merged time section made by merging a preset number of continuous time sections, the modified life log data may be set to indicate one or more estimated activity states included in the respective merged time sections by dividing one or more estimated activity states to the respective merged time sections.

For example, in a case in which the modified life log data having the merged time section having the intervals of thirty minutes illustrated in FIG. 6 is produced by merging the thirty continuous time sections in the life log data having the intervals of one minute illustrated in FIG. 5, a maximum of thirty estimated activity states may be included in the respective merged time sections of the modified life log data, and the modified life log data may be set to indicate the maximum of thirty estimated activity states included in the respective merged time sections by dividing the maximum thirty estimated activity states to the respective merged time sections.

According to the exemplary embodiment, the modified life log data produced in S230 may be data that indicate the respective estimated activity states by dividing the respective estimated activity states to preset colors based on a duration time of at least one estimated activity state for each merged time section.

Now, the exemplary embodiment in which when the merged time section of the modified life log data has the intervals of thirty minutes, the estimated activity state is indicated by being divided to preset colors based on a duration time of one or more estimated activity states included in the respective merged time sections will be described still with reference to FIG. 6.

For example, as illustrated in FIG. 6, a first color, which is a color that indicates a duration time of thirty minutes of the first estimated activity state with respect to the first estimated activity state continued for a total of thirty minutes, may be indicated in a 15th merged time section.

Similarly, as illustrated in FIG. 6, a second color, which is a color that indicates a duration time of three minutes of the second estimated activity state with respect to the second estimated activity state continued for a total of three minutes, may be indicated in a 25th merged time section, and a third color, which is a color that indicates a duration time of 27 minutes of the third estimated activity state with respect to the third estimated activity state continued for a total of 27 minutes, may be indicated.

Here, the colors such as blue, red, and the like, which are set for each duration time of the estimated activity state and illustrated in the form of vertical bars at the right side in FIG. 6, are one exemplary embodiment, and the modified life log data according to the exemplary embodiment of the present disclosure may use various types of colors in order to distinguish one or more estimated activity states included in the respective merged time sections, and the modified life log data according to the exemplary embodiment of the present disclosure are not limited to the colors illustrated in the form of vertical bars at the right side in FIG. 6.

According to the exemplary embodiment, the modified life log data, which are produced in S230, may be data that indicate estimated activity state vectors indicating duration times of at least one estimated activity state for each merged time section.

For example, the estimated activity state vector may mean a vector that has dimensions as many as the number of estimated activity states included in the modified life log data and has a value as a duration time of the respective estimated activity state.

For example, in a case in which a total of nine estimated activity states are included in the modified life log data, the estimated activity state vector may be indicated in the form of a duration time of the first estimated activity state, a duration time of the second estimated activity state, . . . , a duration time of the ninth estimated activity state.

For example, as illustrated in FIG. 6, the estimated activity state vector with respect to the 15th merged time section may be indicated in the form of 30, 0, 0, 0, 0, 0, 0, 0, and 0, and the estimated activity state vector with respect to the 25th merged time section may be indicated in the form of 0, 3, 27, 0, 0, 0, 0, and 0.

Now, step S250 will be described still with respect to FIG. 2.

In step S250, the similarity calculating unit 130 calculates life log similarity among the plurality of modified life log data by comparing the plurality of modified life log data for each merged time section.

According to the exemplary embodiment, step S250 may include steps of calculating similarity for each section which is similarity among estimated activity state vectors of the respective plurality of modified life log data in respect to identical merged time sections and different merged time sections of the plurality of modified life log data, selecting a maximum value of the similarity for each section, as maximum similarity for each section, for each merged time section based on any one merged time section, and calculating the life log similarity by using an average value of the selected maximum similarity for each section.

Here, the step of calculating the similarity for each section, the step of selecting the maximum similarity for each section, and the step of calculating the life log similarity, which are included in step S250, will be specifically described below with reference to FIG. 3, and the overlapping description will be omitted.

Now, an exemplary embodiment of step S250 will be described in more detail with reference to FIG. 3.

FIG. 3 is a flowchart for explaining the step of calculating the life log similarity among the plurality of modified life log data in the method for calculating similarity of life log data according to the exemplary embodiment of the present disclosure.

As illustrated in FIG. 3, the exemplary embodiment of step S250 includes step S251 of calculating the similarity for each section of the respective plurality of modified life log data, step S253 of calculating the weighted similarity for each section by multiplying the similarity for each section by the weight for each section, step S255 of selecting the maximum value of the weighted similarity as the maximum weighted similarity for each section, and step S257 of calculating the life log similarity by using the average value of the maximum weighted similarity for each section.

For example, the exemplary embodiment of step S250 illustrated in FIG. 3 may be an exemplary embodiment which includes a step of calculating the similarity for each section included in step S250 illustrated in FIG. 2, a step of selecting the maximum similarity for each section, and a step of calculating the life log similarity, and further includes step S253.

In step S251, the similarity calculating unit 130 calculates the similarity for each section which is the similarity between the estimated activity state vectors of the respective plurality of modified life log data in respect to the identical merged time sections and the different merged time sections of the respective plurality of modified life log data.

For example, in step S251, the similarity calculating unit 130 may calculate the similarity for each section between the estimated activity state vector for each merged time section of first modified life log data which are reference modified life log data that serve as a comparison reference among the plurality of modified life log data and the estimated activity state vector for each merged time section of second modified life log data which are modified life log data that serves as a comparison object among the plurality of modified life log data.

For example, in step S251, in a case in which the first modified life log data and the second modified life log data have 48 merged time sections, respectively, the similarity calculating unit 130 may calculate 48×48 similarity for each sections, respectively.

According to the exemplary embodiment, the similarity for each section may be calculated based on cosine similarity between the estimated activity state vectors of the respective plurality of modified life log data.

For example, in a case in which the similarity for each section is calculated based on the cosine similarity between the estimated activity state vectors of the respective plurality of modified life log data, the similarity for each section may be calculated by means of the following Expression 1.

$$\text{Similarity} = \cos(\theta) = \frac{\vec{A} \cdot \vec{B}}{\|\vec{A}\| \|\vec{B}\|} \quad \text{[Expression 1]}$$

In this case, $\vec{A}$ is an estimated activity state vector with respect to a particular merged time section of the first modified life log data, and $\vec{B}$ is an estimated activity state vector with respect to a particular merged time section of the second modified life log data.

According to the exemplary embodiment, both of $\vec{A}$ and $\vec{B}$, which are the respective estimated activity state vectors, are positive vectors, and as a result, the calculated similarity for each section may have a value between 0 and 1.

According to the exemplary embodiment, the similarity for each section between the estimated activity state vectors of the respective plurality of modified life log data may be calculated by utilizing various types of similarity calculating methods or error calculating methods such as a relative (percent) accuracy method, a cross correlation method, a convolution method, a residual sum of squares calculating method, a rood mean square calculating method, a least absolute deviation calculating method, and a mean absolute error calculating method.

Now, an exemplary embodiment of step S251 will be described with reference to FIGS. 3 and 7 together, as an example in which in step S251, a total of 48×48 similarity for each section is calculated, which is similarity between the estimated activity state vectors of the modified life log data in respect to a particular date (Jul. 9, 2016) having 48 merged time sections and the modified life log data in respect to another date (Jul. 10, 2016) having 48 merged time sections.

FIG. 7 is a view for explaining the exemplary embodiment of the similarity for each section calculated by the method and the apparatus for calculating similarity of life log data according to the exemplary embodiment of the present disclosure.

In the case of the aforementioned example, a result of calculating a total of 48×48 similarity for each section in step S251 may be shown as illustrated in FIG. 7.

In this case, FIG. 7 illustrates that the similarity for each section is indicated by utilizing colors illustrated in the form of vertical bars at the right side in FIG. 7 for convenience in distinguishing the similarity for each section having a value between 0 and 1, but the similarity for each section according to the exemplary embodiment of the present disclosure is not limited to the colors illustrated in the form of vertical bars at the right side in FIG. 7.

In the case of the aforementioned example, a result of calculating the similarity for each section in step S251 may be shown as illustrated in FIG. 7, and the similarity for each section between the estimated activity state vector of the 15th merged time section of the modified life log data in respect to the particular date (Jul. 9, 2016) and the estimated activity state vector of the 10th merged time section of the modified life log data in respect to another date (Jul. 10, 2016) may be calculated to 1.

Step S253 will be described with reference back to FIG. 3.

In step S253, the similarity calculating unit 130 calculates the weighted similarity for each section by multiplying the similarity for each section by a preset weight for each section.

According to the exemplary embodiment, the preset weight for each section may be set based on a time difference among the merged time sections of the respective plurality of modified life log data.

For example, the preset weight for each section may be set based on a time difference between a particular merged time section of particular modified life log data, which is an object for calculating the respective similarity for each section calculated in step S251 and a particular merged time section of another modified life log data.

For example, the reason why the preset weight for each section is provided to the similarity for each section in step S253 is to calculate similarity in accordance with an occurrence time between the one or more estimated activity states included in the respective plurality of modified life log data.

For example, the first estimated activity state indicated in the first merged time section of the particular modified life log data and the first estimated activity state indicated in the first merged time section of another modified life log data are the same estimated activity state occurring in the similar time zone, and as a result, high similarity needs to be calculated. The first estimated activity state indicated in the first merged time section of the particular modified life log data and the first estimated activity state indicated in the 25th merged time section of another modified life log data are the same estimated activity state, but the estimated activity states which occur in the different time zone, and as a result, low similarity needs to be calculated.

For example, in a case in which the particular user gets to sleep at 3 am at the particular date, the sleep may mean "a sleep at night", and in a case in which the particular user gets to sleep at 3 pm at another date, the sleep may mean "a nap", and as a result, in step S253, the similarity calculating unit 130 may multiply the similarity for each section by the preset weight for each section based on the time difference between the merged time sections of the respective plurality of modified life log data.

Now, an exemplary embodiment of the weight for each section will be described with reference to FIGS. 3 and 8 together.

FIG. 8 is a view for explaining the exemplary embodiment of the weight for each section in the method and the apparatus for calculating similarity of life log data according to the exemplary embodiment of the present disclosure.

For example, the preset weight for each section may have a minimum value in a case in which the time difference between the merged time sections of the respective plurality of modified life log data is 12 hours, and may have a maximum value in a case in which the time difference is 0 hour or 23 hours 59 minutes.

According to the exemplary embodiment, the preset weight for each section may be increased linearly or nonlinearly when the time difference between the merged time sections is decreased to 0 hour based on 12 hours or increased to 23 hours 59 minutes based on 12 hours.

As illustrated in FIG. 8, the weight for each section according to the exemplary embodiment may be set to have a minimum value in a case in which the time difference between the particular merged time section included in the particular modified life log data and the particular merged time section included in another modified life log data is 12 hours, and have a maximum value in a case in which the time difference is 0 hour or 23 hours 59 minutes.

The reason is that because there are 24 hours in a day, in a case in which the time difference between the particular merged time section included in the particular modified life log data and the particular merged time section included in another modified life log data is 12 hours, the time difference may mean a time zone in which the morning and the afternoon are changed, and in a case in which the time difference is 0 hour or 23 hours 59 minutes, the time difference may mean the similar time zone.

In this case, the weight for each section, which is linearly increased when the time difference is increased or decreased based on a case in which the time difference illustrated in FIG. 8 is 12 hours, is an exemplary embodiment, and the weight for each section according to the exemplary embodiment of the present disclosure may have various types of shapes in which the weight for each section has a minimum value in a case in which the time difference is 12 hours, and has a maximum value in a case in which the time difference is 0 hour or 23 hours 59 minutes, and the weight for each section is nonlinearly increased when the time difference is increased or decreased based on a case in which the time difference is 12 hours.

Now, an exemplary embodiment of step S253 will be described with reference to FIGS. 3 and 9 together, as an example in which in step S253, a total of 48×48 similarity for each section, which is similarity between the estimated activity state vectors of the modified life log data in respect to the particular date (Jul. 9, 2016) having 48 merged time sections and the modified life log data in respect to another date (Jul. 10, 2016) having 48 merged time sections, is multiplied by the weight for each section based on the time difference between the merged time sections.

FIG. 9 is a view for explaining the exemplary embodiment of the weighted similarity for each section calculated by the method and the apparatus for calculating similarity of life log data according to the exemplary embodiment of the present disclosure.

In the case of the aforementioned example, a result of calculating the weighted similarity for each section by multiplying the 48×48 similarity for each section by the weight for each section in step S253 may be shown as illustrated in FIG. 9.

In this case, FIG. 9 illustrates that the weighted similarity for each section is indicated by utilizing colors illustrated in the form of vertical bars at the right side in FIG. 9 for convenience in distinguishing the weighted similarity for each section having a value between 0 and 1, but the weighted similarity for each section according to the exemplary embodiment of the present disclosure is not limited to the colors illustrated at the right side in FIG. 9.

In the case of the aforementioned example, a result of calculating the weighted similarity for each section in step S253 may be shown as illustrated in FIG. 9, and for example, the weighted similarity for each section may be calculated to 0 by multiplying the weight for each section by the similarity for each section between the estimated activity state vector of the 20th merged time section of the modified life log data in respect to the particular date (Jul. 9, 2016) and the estimated activity state vector of the 20th merged time section of the modified life log data in respect to another date (Jul. 10, 2016) may be calculated to 0.

According to the exemplary embodiment, the weighted similarity for each section in a region of a right upper end based on a diagonal line that connects a left upper end and a right lower end in FIG. 9 is calculated to 0, and the reason is that the time difference between the merged time sections of the respective plurality of modified life log data is in a negative region, but the present disclosure is not limited thereto.

Step S255 will be described with reference back to FIG. 3.

In step S255, the similarity calculating unit 130 selects a maximum value of the weighted similarity for each section for each merged time section based on any one merged time section, as the maximum weighted similarity for each section.

Now, an exemplary embodiment of step S255 will be described with reference to FIGS. 3 and 10 together, as an example in which in step S255, a total of 48×48 similarity for each section, which is similarity between the estimated activity state vectors of the modified life log data in respect to the particular date (Jul. 9, 2016) having 48 merged time sections and the modified life log data in respect to another date (Jul. 10, 2016) having 48 merged time sections, is multiplied by the weight for each section based on the time difference between the merged time sections so as to select a maximum value of the calculated weighted similarity for each section as the maximum weighted similarity for each section.

For example, in FIG. 10, the maximum value of the weighted similarity for each section for each merged time section is selected as the maximum weighted similarity for each section based on the respective merged time sections of the modified life log data in respect to another date (Jul. 10, 2016) from the weighted similarity for each section illustrated in FIG. 9.

Step S257 will be described with reference back to FIG. 3.

In step S257, the similarity calculating unit 130 calculates the life log similarity by using an average value of the selected maximum weighted similarity for each section.

For example, the life log similarity may mean similarity between the plurality of modified life log data.

According to the exemplary embodiment, the life log similarity may be calculated by means of the following Expression 2.

$$S = \frac{\sum_{i=1}^{n} S_i}{n} \qquad \text{[Expression 2]}$$

In this case, S means the life log similarity, si means maximum weighted similarity with respect to an ith merged time section of particular modified life log data, and n is the number of merged time sections of the particular modified life log data.

For example, the estimated activity states, which is used by the method and the apparatus for calculating similarity of life log data according to the exemplary embodiment of the present disclosure in order to produce (S210) the plurality of life log data on a daily basis, may include a plurality of detailed estimated activity states which is divided based on at least one additional information among weather information, temperature information, humidity information, illumination intensity information, carbon dioxide amount information, user's heart rate information.

For example, in a case in which the life log data producing unit 110 produces a plurality of life log data by using weather information among the additional information in order to produce the plurality of life log data on a daily basis, the life log data producing unit 110 may produce the plurality of life log data by utilizing all of the particular user's position information at a particular time, the particular user's motion state information at a particular time, and weather information at a particular time.

For example, in a case in which the particular user's position information at a particular time coincides with position information of a movie theater which is stored in advance, the motion state information is the steady state information, and the weather information is information showing that it's rainy, the life log data producing unit 110 may select a detailed estimated activity state of the particular user such as estimating that the particular user watches a movie in the movie theater when it's rainy at a particular time.

For example, the method and the apparatus for calculating similarity of life log data according to the exemplary embodiment of the present disclosure may calculate the life log similarity by comparing modified life log data up to the current time today with modified life log data at a particular date in the past for each merged time section.

In this case, the user may recognize similarity between the life log data up to the current time today and the life log data at a particular date in the past when there is a bad lifestyle habit, and as a result, the user's attention is drawn to the bad lifestyle habit, thereby eliminating the bad lifestyle habit.

For example, in a case in which the life log data up to the current time today is similar to the life log data at a particular date in the past when the user had a late-night snack, it is possible to determine that the user is more likely to have a late-night snack today.

For example, in a case in which the life log data up to the current time today is similar to the life log data at a particular date in the past when the amount of activity is insufficient, the user may expect that the amount of activity today will be insufficient.

Now, the life log similarity, which is calculated by utilizing the method and the apparatus for calculating similarity of life log data according to the exemplary embodiment of the present disclosure, will be described with reference to FIG. 11.

FIG. 11 is a view for explaining the life log similarity among the plurality of life log data compared by the method and the apparatus for calculating similarity of life log data according to the exemplary embodiment of the present disclosure.

In this case, a first day DAY1, a second day DAY2, and a fifth day DAY5 may mean the days the user did not go hiking, and a third day DAY3 and a fourth day DAY4 may mean the days the user went hiking.

As illustrated in FIG. 11, the life log similarity of 100% is shown as a result of calculating the life log similarity at the same date, the life log similarity between the third day DAY3 and the fourth day DAY4, which are the day the user went hiking, is the life log similarity of 70.20% as a result of calculating the life log similarity of the third day DAYS based on the fourth day DAY4, and the life log similarity of 78.07% as a result of calculating the life log similarity of the fourth day DAY4 based on the third day DAY3.

While the exemplary embodiments according to the present disclosure have been described above, it will be understood by those skilled in the art that the exemplary embodiments may be modified in various forms, and various variants and modifications may be implemented without departing from the claims of the present disclosure.

What is claimed is:

1. A method of calculating similarity of life log data, the method comprising:
    producing, by a life log data producing unit, a plurality of life log data on a daily basis, in which at least one estimated activity state is indicated for each predetermined time section, by matching information based on a combination of a user's position information per time period and a user's motion state information per time period with an estimated activity table in which the user's estimated activity states are defined in advance;
    converting, by a modified life log data producing unit, the plurality of life logs data into a plurality of modified life log data which is indicated for each merged time section made by accumulating a preset number of continuous time sections, wherein the modified life log data are data that indicate estimated activity state vectors indicating a duration time of at least one estimated activity state for each merged time section; and
    calculating, by a similarity calculating unit, life log similarity among the plurality of modified life log data based on comparison with each other merged time section in the plurality of modified life log data.

2. The method according to claim 1, wherein the motion state information is information which indicates the user's motion state at a particular time which is selected based on the user's motion intensity, and the motion state information includes at least one state information among steady state information, sleeping state information, walking state information, and running state information.

3. The method according to claim 1, wherein the calculating of the similarity includes:
    calculating similarity for each section which is similarity between the estimated activity state vectors of the respective plurality of modified life log data in respect to identical merged time sections and different merged time sections of the respective plurality of modified life log data;
    selecting a maximum value of the similarity for each section as maximum similarity for each section for each merged time section based on any one of the merged time sections; and
    calculating the life log similarity by using an average value of the selected maximum similarity for each section.

4. The method according to claim 3, wherein the similarity for each section is calculated based on cosine similarity between the estimated activity state vectors of the respective plurality of modified life log data.

5. The method according to claim 1, wherein the calculating of the similarity includes:
    calculating similarity for each section which is similarity between the estimated activity state vectors of the respective plurality of modified life log data in respect to identical merged time sections and different merged time sections of the respective plurality of modified life log data;
    calculating weighted similarity for each section by multiplying the similarity for each section by a preset weight for each section;
    selecting a maximum value of the weighted similarity for each section as maximum weighted similarity for each section for each merged time section based on any one of the merged time sections; and
    calculating the life log similarity by using an average value of the selected weighted maximum similarity for each section.

6. The method according to claim 5, wherein the preset weight for each section is set based on a time difference between the merged time sections of the respective plurality of modified life log data.

7. The method according to claim 6, wherein the preset weight for each section has a minimum value in a case in which the time difference between the merged time sections of the respective plurality of modified life log data is 12 hours, and has a maximum value in a case in which the time difference is 0 hour or 23 hours 59 minutes, and the preset weight for each section is increased linearly or nonlinearly when the time difference between the merged time sections is decreased to 0 hour based on 12 hours or increased to 23 hours 59 minutes based on 12 hours.

8. The method according to claim 5, wherein the similarity for each section is calculated based on cosine similarity between the estimated activity state vectors of the respective plurality of modified life log data.

9. The method according to claim 1, wherein the modified life log data are data that indicate the respective estimated activity states by dividing the respective estimated activity states to preset colors based on a duration time of at least one estimated activity state for each merged time section.

10. The method according to claim 1, wherein the estimated activity state includes a plurality of detailed estimated activity states divided based on at least one additional information among weather information, temperature information, humidity information, illumination intensity information, carbon dioxide amount information, and the user's heart rate information.

11. An apparatus for calculating similarity of life log data, the apparatus comprising:

a computer processor; and a data storage device that stores computer-readable codes executable by the computer processor, the computer readable codes defining functional units which include:

a life log data producing unit which produces a plurality of life log data on a daily basis, in which at least one estimated activity state is indicated for each predetermined time section, by matching information based on a combination of a user's position information per time period and a user's motion state information per time period with an estimated activity table in which the user's estimated activity states are defined in advance;

a modified life log data producing unit which converts the plurality of life logs data into a plurality of modified life log data which is indicated for each merged time section made by accumulating a preset number of continuous time sections, wherein the modified life to data are data that indicate estimated activity state vectors indicating a duration time of at least one estimated activity state for each merged time section; and a similarity calculating unit which calculates life log similarity among the plurality of modified life log data based on comparison with each other merged time section in the plurality of modified life log data.

12. The apparatus according to claim 11, wherein the similarity calculating unit calculates similarity for each section which is similarity between the estimated activity state vectors of the respective plurality of modified life log data in respect to identical merged time sections and different merged time sections of the respective plurality of modified life log data, selects a maximum value of the similarity for each section as maximum similarity for each section for each merged time section based on any one of the merged time sections, and calculates the life log similarity by using an average value of the selected maximum similarity for each section.

13. The apparatus according to claim 11, wherein the similarity calculating unit calculates similarity for each section which is similarity between the estimated activity state vectors of the respective plurality of modified life log data in respect to identical merged time sections and different merged time sections of the respective plurality of modified life log data, calculates weighted similarity for each section by multiplying the similarity for each section by a preset weight for each section, selects a maximum value of the weighted similarity for each section as maximum weighted similarity for each section for each merged time section based on any one of the merged time sections, and calculates the life log similarity by using an average value of the selected weighted maximum similarity for each section.

14. The apparatus according to claim 13, wherein the preset weight for each section is set based on a time difference between the merged time sections of the respective plurality of modified life log data.

* * * * *